(12) United States Patent
Vogt et al.

(10) Patent No.: US 10,307,496 B2
(45) Date of Patent: Jun. 4, 2019

(54) METHOD FOR STERILIZATION OF AQUEOUS POLYSACCHARIDE SOLUTIONS AND STERILE AQUEOUS POLYSACCHARIDE SOLUTIONS

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 0 days.

(21) Appl. No.: 15/375,666

(22) Filed: Dec. 12, 2016

(65) Prior Publication Data
US 2017/0173192 A1    Jun. 22, 2017

(30) Foreign Application Priority Data
Dec. 22, 2015 (DE) .................. 10 2015 226 456

(51) Int. Cl.
| | | |
|---|---|---|
| A61L 2/00 | (2006.01) |
| A61K 47/36 | (2006.01) |
| A61K 47/12 | (2006.01) |
| A61K 47/02 | (2006.01) |
| C08L 1/28 | (2006.01) |
| C08L 3/08 | (2006.01) |
| C08L 5/00 | (2006.01) |
| C08L 5/08 | (2006.01) |
| C08B 11/02 | (2006.01) |
| C08B 11/12 | (2006.01) |
| C08B 37/08 | (2006.01) |

(52) U.S. Cl.
CPC .......... *A61L 2/0082* (2013.01); *A61K 47/02* (2013.01); *A61K 47/12* (2013.01); *A61K 47/36* (2013.01); *C08L 1/284* (2013.01); *C08L 1/286* (2013.01); *C08L 3/08* (2013.01); *C08L 5/00* (2013.01); *C08L 5/08* (2013.01); *A61L 2202/21* (2013.01); *C08B 11/02* (2013.01); *C08B 11/12* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 4,782,046 A | * | 11/1988 | Brown .............. C08B 37/0072 514/54 |
| 5,093,487 A | | 3/1992 | Brown et al. |
| 5,316,926 A | | 5/1994 | Brown et al. |
| 7,956,094 B2 | | 6/2011 | Alupei et al. |
| 8,283,463 B2 | | 10/2012 | Liu et al. |
| 9,457,110 B2 | | 10/2016 | Vogt |
| 9,717,821 B2 | | 8/2017 | Schutte et al. |
| 2006/0292030 A1 | | 12/2006 | Odermatt et al. |
| 2008/0255241 A1 | | 10/2008 | Alupei et al. |
| 2016/0228494 A1 | | 8/2016 | Schwach et al. |
| 2016/0346426 A1 | | 12/2016 | Vogt |

FOREIGN PATENT DOCUMENTS

| | | |
|---|---|---|
| CA | 2794358 C | 5/2013 |
| DE | 102005017845 A1 | 10/2006 |
| EP | 0 228 698 A2 | 7/1987 |
| EP | 0 364 842 A1 | 4/1990 |
| EP | 1 730 473 A2 | 12/2006 |
| EP | 2 596 812 B1 | 5/2013 |
| GB | 820149 * | 9/1959 |
| GB | 1090492 A | 11/1967 |
| JP | S60-13384 A | 7/1985 |
| JP | 2013-106947 A | 6/2013 |
| JP | 2014-518250 A | 7/2014 |
| JP | 2016-534040 A | 11/2016 |
| WO | 03/002159 A1 | 1/2003 |
| WO | 2015/052204 A1 | 4/2015 |

OTHER PUBLICATIONS

Phosphate Buffered Saline System at https://www.sigmaaldrich.com/content/dam/sigma-aldrich/docs/Sigma/Datasheet/pbs1dat.pdf (retrieved from the internet Apr. 12, 2018) (Year: 2018).*
Liao et al. in Drug Delivery 12:327-342 (2005) (Year: 2005).*
Chemistry Laboratory at http://generalchemistrylab.blogspot.com/2011/12/neutralization-of-polyprotic-acid-with.html. (retrieved from the internet Apr. 13, 2018) (Year: 2012).*
German Office Action dated Mar. 17, 2017 issued by the German Patent Office for corresponding German Application No. 10 2015 226 456.4.
Australian Examination Report dated May 30, 2017 issued by the Australian Patent Office for corresponding Australian Application No. 2016273811.
English Translation of Japanese Office Action dated Oct. 24, 2017 issued by the Japanese Patent Office for corresponding Japanese Application No. 2016-238159.
European International Search Report dated May 16, 2017.
Canadian Office Action dated Jan. 10, 2018 issued by the Canadian Patent Office for corresponding Canadian Application No. 2,950,709.

* cited by examiner

*Primary Examiner* — Dennis Heyer
(74) *Attorney, Agent, or Firm* — Norris McLaughlin, P.A.

(57) ABSTRACT

Sterilization method according to which an aqueous polysaccharide solution is stored in the presence of a lactone and a buffer system for a period of at least 24 hours, and a sterile polysaccharide solution produced in this way.

15 Claims, No Drawings

METHOD FOR STERILIZATION OF AQUEOUS POLYSACCHARIDE SOLUTIONS AND STERILE AQUEOUS POLYSACCHARIDE SOLUTIONS

This application claims foreign priority benefit under 35 U.S.C. § 119 of German Patent Application No. 10 2015 226 456.4, filed Dec. 22, 2015, the disclosures of which are incorporated herein by reference.

The subject matter of the invention is a method for sterilization of aqueous polysaccharide solutions as well as the polysaccharide solutions produced by means of said method.

BACKGROUND OF THE INVENTION

Arthrosis (Arthrosis deformans) is a common degenerative disease of the joints. It involves damage (erosion) to the cartilage surfaces, detachment of cartilage particles, and inflammation of the synovial membrane caused by the cartilage particles. In cases of mild and moderate arthrosis, attempts have been made in recent years to use an intra-articular injection of hyaluronic acid (visco-supplementation) to improve the patients' pain status and to concurrently reduce the progression of the arthrosis.

Hyaluronic acid is a natural ingredient of the synovial fluid (joint liquid). Hyaluronic acid acts as a lubricant in the synovial fluid. It is particularly advantageous that aqueous hyaluronic acid solutions are visco-elastic. This results in very good lubricant and gliding properties.

Based on the advantageous lubricant properties, hyaluronic acid solutions have been in use for visco-supplementation for approximately the past two decades. The current state of the prior art is the use of hyaluronic acid, which is produced by fermentation and is used in the form of a sterile aqueous hyaluronic acid solution. Besides, the use of water-soluble cellulose derivatives, such as carboxymethylcellulose and methylcellulose, starch derivatives, such as hydroxyethyl starch, for visco-supplementation is also feasible on principle.

Thus far, it is common to sterilize aqueous hyaluronic acid solutions by exposure to gamma radiation. Doses of 25 kGy or more are common in this context. This sterilization is done on finally packaged hyaluronic acid solution.

However, the exposure to gamma radiation is associated with grave disadvantages. In addition to degradation of the polymer chains by means of which more or less low-molecular degradation products are produced depending on the dose of gamma radiation, side reactions leading to the discolouration of the hyaluronic acid solutions can occur as well. Another disadvantage of the use of gamma radiation is that the common gamma sources have a spherical radiation field. As a result, the incident doss can vary as a function of the position of the object to be sterilized. This results in uneven polymer degradation, which possibly is associated with inhomogeneities of the final viscosity. A reproducible final viscosity of the sterilized hyaluronic acid solutions is virtually impossible to attain. Moreover, the gamma radiation can lead to brittling of the packaging means, which usually are disposable plastic syringes.

Similar disadvantages are associated with steam sterilization of aqueous hyaluronic acid solutions, which can lead to damage to the hyaluronic acid and the plastic packaging means.

Due to the relatively high viscosity of the solutions, sterile filtration of aqueous hyaluronic acid solutions is basically not feasible or only with an inordinate effort. Moreover, sterile filtration removes microbial life forms only from a certain size. Viruses cannot be removed or inactivated by sterile filtration.

Aside from said physical methods, it is customary to use chemical compounds for sterilization of medical products. These include formaldehyde, glutardialdehyde, o-phthaldialdehyde. The sterilization using aldehydes is disadvantageous in that these need to be removed again after the sterilization order to prevent damage during the use in humans. This precludes sterilization with aldehydes in the case of aqueous hyaluronic acid solutions in their final packages. Aldehydes cannot be removed again from hyaluronic acid solutions in their final packages.

Oxidising agents, such as hydrogen peroxide, performic acid, peracetic acid, hypochloride, and hypochloride-releasing substances, such as chloramine T 2 or trichloroisocyanuric acid, are very effective sterilization means. These agents are disadvantageous in that they cause significant oxidative degradation of the dissolved hyaluronic acid. Moreover, non-reacted residues of the oxidising agents may remain in the hyaluronic acid solution in its final packaging and may possibly have a local toxic effect.

It is known from pharmaceutical industry that aqueous protein solutions, such as, e.g., vaccines, are very sensitive to the effects of oxidising sterilization agents and various physical sterilization methods, for example sterilization with gamma radiation. For this reason, these aqueous protein solutions are subjected to sterile filtration first and then have small amounts of β-propiolactone added to inactivate viruses. β-propiolactone acylates the amino groups of the DNA/RNA or proteins of the viruses. The water that is present as solvent is capable of slowly decomposing β-propiolactone such that no active β-propiolactone is present any longer in aqueous protein solutions after just a short period of time. It is known thus far that gaseous β-propiolactone can irreversibly inactivate endospores (R. K. Hoffmann, B. Warshowsky: Beta-Propiolactone Vapor as a Disinfectant. Appl. Microbiol. 1958 September; 6(5): 358-362). Moreover, it is known that β-propiolactone inactivates endospores in non-aqueous organic monomers/monomer mixtures and pasty cements containing organic monomers (EP 2 596 812 B1).

However, aside from the vegetative forms, micro-organisms also have generative forms, such as endospores. These generative survival forms of micro-organisms are formed by gram-positive bacteria, in particular of the *Bacillus* and *Clostridium* genera, as a means of persisting during unfavourable living conditions. In their resting state, endospores have no active metabolism and possess a multi-layered spore capsule that largely protects the core of the spore from the action of chemicals and other environmental effects. This renders spores extremely resistant to the action of heat and chemicals (Borick, P. M.: Chemical sterilizers. Adv. Appl. Microbiol. 10 (1968) 291-312; Gould, G. W.: Recent advances in the understanding of resistance and dormancy in bacterial spores. J. Appl. Bacteriol. 42 (1977) 297-309; Gould, G. W.: Mechanisms of resistance and dormancy. p. 173-209. In Hurst, A. and Gould, G. W. (ed.), The bacterial spore. vol. 2 Academic Press, Inc. New York, 1983). Due to their high resistance, endospores are used as bio-indicators for validation and control of the efficacy of sterilization processes. This is based on the assumption that the inactivation of endospores is indicative of all vegetative microbial forms of life being killed. Endospores of gram-positive bacteria are classified in international resistance class III. Resistance classes I include non-spore-forming bacteria and vegetative forms of spore-forming bacteria and resistance class II includes spores that are killed within a few minutes in a flow of steam at 105° C. In accordance with DAB 2008 (Deutsches Arzneimittelbuch), all micro-organisms of resistance classes I-III must be killed or inactivated irreversibly.

The object of the invention is to develop a method for the sterilization of aqueous polysaccharide solutions. Said method is to enable a sterilization without significant degradation of the dissolved polysaccharide polymers.

Moreover, the sterilization method to be developed shall be suitable for sterilization of aqueous polysaccharide solutions stored in their final packages, including the internal walls of the packaging means that contact the aqueous polysaccharide solution. The sterilization methods to be developed shall safely inactivate microorganisms of resistance level III.

In the scope of the invention, sterility shall be understood to mean a state that is free of viable micro-organisms in accordance with EN 556-1:2001.

SUMMARY OF THE INVENTION

The object of the invention is solved according to claim 1 through a method for the sterilization of aqueous polysaccharide solutions. According to the invention, a β-lactone is added to an aqueous solution of a polysaccharide in the presence of a buffer, and the mixture is stored at a temperature of 4° C. to 40° C. for a period of at least 24 hours.

A preferred method is characterised by
a) dissolving at least one polysaccharide in water;
b) adding at least 0.5% by weight β-lactone to the aqueous polysaccharide solution produced in a)
c) storing the mixture at a temperature of 4° C. to 40° C. for a period of at least 24 hours, whereby
the aqueous solution contains a buffer system whose buffering capacity is sufficient to buffer the 3-hydroxypropanoic acid generated by hydrolysis of the β-lactone such that the pH value of the sterilized aqueous polysaccharide solution is equal to that of the unsterilized polysaccharide solution.

The object is also met according to claim 14 through a sterile polysaccharide solution produced according to any one of the methods above.

DETAILED DESCRIPTION

It was evident, surprisingly, that an aqueous polysaccharide solution can be sterilized through the use of a method according to claim 1 with just minimal polymer degradation proceeding. This means that the ratio of the reduced specific viscosity of the sterilized polysaccharide solution and the reduced specific viscosity of the unsterile polysaccharide solution can be maintained at more than/equal to 0.8. In determining this ratio, it is of no importance whether the reduced specific viscosity, the dynamic viscosity or the kinematic viscosity is measured. In the case of aqueous polysaccharide solutions, that are amenable to gel permeation chromatography, the ratio of the number average molar mass of the sterilized polysaccharide and the number average molar mass of the unsterilized polysaccharide can be maintained at more than/equal to 0.8. Moreover, the sterilization method according to the invention does not cause any discolouration due to side reactions during the sterilization process.

Endospores of resistance level III suspended in aqueous polysaccharide solutions are inactivated by means of the method according to the invention through the action of β-lactone. In this context, the polysaccharide solutions contain a buffer of sufficient capacity to buffer the 3-hydroxypropionic acid released by the hydrolysis of the β-lactone such that the pH value of the sterilized polysaccharide solutions is equal to the pH value of the previously unsterile polysaccharide solutions. It is preferable in this context to use buffer in the same amount as the β-lactone.

The invention is further based on finding, surprisingly, that β-lactone allows a sterilization of aqueous polysaccharide solutions to be performed in the presence of a buffer without significant polymer degradation of the polysaccharides proceedings during the sterilization. The special advantage of the sterilization according to the invention is that the viscosity of the polysaccharide solutions before and after sterilization stays equal. Referring to the use of aqueous polysaccharide solutions for visco-supplementation, this means that the viscosity of the solutions can be adjusted accurately before the sterilization as there is no change of the viscosity due to the sterilization process. As a result, sterile polysaccharide solutions that are accurately adjusted in terms of the viscosity and the other rheological properties can be provided for visco-supplementation. It is another advantage that there is no discolouration of the aqueous polysaccharide solutions due to the sterilization.

Polysaccharides are carbohydrates in which a large number (at least 10) of monosaccharides is connected to each other by means of a glycosidic bond. Water-soluble polysaccharides in the scope of the present invention are polysaccharides that consist of monosaccharides, disaccharides, further oligomers thereof or derivatives and are linked to each other in the same manner.

According to the invention, the polysaccharides are natural polysaccharides and artificial polysaccharides. According to the invention, derivatives shall be understood to be salts, ethers, esters of the acids or esters, in particular alkali metal salts, particularly sodium and potassium salts. Examples include alginic acid, sodium alginate, hyaluronic acid, the sodium salt of hyaluronic acid, carboxymethylcellulose, the sodium salt of carboxymethylcellulose, hydroxyethylcellulose, cellulose ether, starch, starch ether, guar, chitin, chitosan.

Preferably, the polysaccharide is selected from the group consisting of the sodium salt of hyaluronic acid, the sodium salt of carboxymethylcellulose, hydroxyethylcellulose, hydroxyethyl starch, methylcellulose, and oxidised cellulose.

According to the invention, the polysaccharides can just as well be mixtures of the aforementioned polysaccharides.

The polysaccharides are preferably used in an amount of at least 0.5% by weight. Moreover, there are preferably used in an amount of at most 5% by weight. It is particularly preferable to use polysaccharides in an amount of 1 to 2% by weight. The amount in each case refers to the amount of polysaccharide in water.

The β-lactone can be a compound (a1) that is represented by general formula (I)

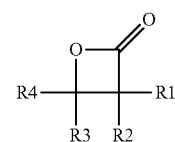

In said formula, R1, R2, R3, and R4, independently of each other, can represent H, a substituted or non-substituted alkyl residue, a halogen residue, a nitro residue or a cyano residue.

The stereochemistry of compounds (a1) is not limited in any way. Preferably, the scope of the invention includes as compound (I) all isomers represented through general formula (I), regardless of their exact configuration.

The alkyl residues can be substituted or non-substituted alkyl residues, independently of each other. The at least one substituent of a substituted alkyl residue is preferably selected from the group consisting of halogen residues, nitro residues, and cyano residues.

The alkyl residues can be saturated or unsaturated alkyl residues, independently of each other. Preferably, an unsaturated alkyl residue comprises at least one carbon-carbon double bond.

The alkyl residues can be branched or unbranched alkyl residues, independently of each other. It is preferable for alkyl residues R1, R2, R3, and R4 to be unbranched alkyl residues.

Independently of each other, the alkyl residues have a main chain length in the range of 1-4 carbon atoms, more preferably a main chain length in the range of 1-2 carbon atoms, and even more preferably one carbon atom.

Fluorine residues, chlorine residues, and bromine residues are preferred halogen residues in general formula (I). Said residues each can represent one or more of residues R1, R2, R3, and R4, independently of each other.

According to a preferred embodiment, residues R1, R2, R3, and R4 each represent H.

According to another preferred embodiment, residue R1 represents a methyl residue and residues R2, R3, and R4 represent H.

According to another preferred embodiment, residues R1, R2, and R3 represent H and residue R4 represents a methyl residue.

According to yet another preferred embodiment, residues R1 and R3 represent H and residues R2 and R4 represent a methyl residue.

According to a particularly preferred embodiment, compound (a1) is β-propiolactone (CAS number 57-57-8).

The β-propiolactone can just as well be a compound (a2) that is a dimer of any of compounds (a1). The stereochemistry of compounds (a2) is not limited in any way.

According to the invention phosphate buffer with a pH value of 7.0-8.0 is preferred as buffer, whereby a phosphate buffer with a pH value of 7.4 is particularly preferred.

In particular the combination of potassium hydrogenphosphate and disodium hydrogenphosphate, the combination of sodium hydrogenphosphate and disodium hydrogenphosphate, the combination of disodium phosphate and phosphoric acid and the combination of trisodium phosphate and sodium hydrogenphosphate, and the combination of trisodium phosphate and phosphoric acid are well-suited for producing the phosphate buffer.

Preferably, all of the components of the phosphate buffer together are dissolved in the aqueous polysaccharide solution at a concentration of more than/equal to 0.5% by weight.

According to the invention, the 3-hydroxypropionic acid produced by the hydrolysis of the β-propiolactone is a component of the buffer.

According to the invention, the 3-hydroxypropanoic acid and the sodium salt of the hyaluronic acid or 3-hydroxypropanoic acid and the sodium salt of the carboxymethylcellulose form a buffer.

It is essential to the invention that the sterilization of the aqueous polysaccharide solution takes place inside the primary packaging means. As a result, no additional effort such as gamma irradiation or irradiation with electrons or autoclaving is required. As a result, substantial production costs can be saved.

It is important for successful sterilization that the aqueous polysaccharide solution and β-propiolactone are mixed right before the aqueous polysaccharide solution is filled into the primary packaging means. This ensures that sufficient sterilization agent is available for sterilization of both the polysaccharide solution and the internal walls of the primary packaging means. In contrast, if the polysaccharide solution and the β-propiolactone are mixed an extended period of time before the primary packaging means gets filled, there may be a loss of β-propiolactone due to hydrolysis generating 3-hydroxypropionic acid depending on the temperature and the time elapsed before the primary packaging means is being filled. This can, in particular, render the sterilization of the internal walls of the primary packaging means questionable.

The scope of the invention includes a sterile aqueous polysaccharide solution produced according to the method according to the invention. Said sterile polysaccharide solution is characterised in that the aqueous polysaccharide solution contains at least one polysaccharide that is at least partially soluble in water, water, and 3-hydroxypropionic acid, and a buffer system.

Moreover, according to the invention, the sterile aqueous polysaccharide solution contains a buffer system consisting of sodium ions, dihydrogenphosphate ions, hydrogenphosphate ions, phosphate ions, 3-hydroxypropionic acid, and 3-hydroxypropionate. Potassium ions may be contained therein as well.

According to the invention, the ratio of the reduced viscosity of the sterilized polysaccharide solution and the reduced viscosity of the non-sterilized polysaccharide solution is more than 0.8.

The scope of the invention also includes the use of the sterile aqueous polysaccharide solution as a means for visco-supplementation and as a pharmaceutical drug carrier in human and veterinary medicine.

The invention is illustrated through the examples presented in the following, though without limiting the scope of the invention.

EXAMPLES

The following polysaccharides and/or polysaccharide derivatives were used in the experiments described hereinafter:

Sodium salt of hyaluronic acid ($M_n$~1.3 million Dalton, Kraeber GmbH),

Sodium salt of carboxymethylcellulose ($M_n$~90,000 Dalton, Sigma-Aldrich),

Methylcellulose (SM-4000, Shin-Etsu-Chemical Co.),

Hydroxyethylcellulose (60SH-4000, Shin-Etsu-Chemical. Co)

A phosphate buffer with a pH value of 7.4 was produced. For this purpose, 1.65 g potassium hydrogenphosphate and 9.71 g disodium hydrogenphosphate dihydrate were dissolved in 1 liter of distilled water.

Example 1

Solutions of the polysaccharides were produced using 30 mL phosphate buffer (pH value 7.4) each.

| Polysaccharide | Concentration of the polysaccharide in the phosphate buffer [wt. %] |
|---|---|
| Sodium salt of hyaluronic acid | 0.25 |
| Sodium salt of carboxymethylcellulose | 2.00 |
| Methylcellulose (SM-4000) | 1.00 |
| Hydroxyethylcellulose (60SH-4000) | 1.00 |

A total of $10^6$ cfu of a spore suspension of *Bacillus atropheus* were added to 5 mL each of the polysaccharide solutions in a sterile 25 mL plastic tube. Then the spores were suspended homogeneously using a vortex mixer. Subsequently, 0.5% by weight, 1.0% by weight, and 2.0% β-propiolactone were added to 5 mL each of the polysaccharide solutions previously mixed with the spores. The sample was then homogenised again in a vortex mixer. Polysaccharide solutions not treated with β-propiolactone were used as positive control. After 48 hours of storage at room temperature, the of the polysaccharide solutions were tested for sterility in accordance with DIN EN ISP 11737, part 2. The assays were done in duplicate.

| Polysaccharide | Concentration of the polysaccharide in the phosphate buffer [wt. %] | Result of the test of sterility Concentration β-propiolactone [wt. %] | | | |
|---|---|---|---|---|---|
| | | 0.0 (Positive control) | 0.5 | 1.0 | 2.0 |
| Sodium salt of hyaluronic acid | 0.25 | +/+ | +/– | –/– | –/– |
| Sodium salt of carboxymethyl-cellulose | 2.00 | +/+ | –/– | –/– | –/– |
| Methylcellu-lose (SM-4000) | 1.00 | +/+ | –/– | –/– | –/– |
| Hydroxyethyl-cellulose (60SH-4000) | 1.00 | +/+ | –/– | –/– | –/– |

(+) growth (–) no growth

The polysaccharide solutions sterilized with β-propiolactone show no discolouration whatsoever as compared to the untreated polysaccharide solutions used as positive control.

Example 2

The following polysaccharides were used in the experiments described hereinafter:

NaHya 1: Sodium salt of hyaluronic acid ($M_n$~1.0 million Dalton, Sigma-Aldrich)

NaHya 2: Sodium salt of hyaluronic acid ($M_n$~1.3 million Dalton, Kraeber GmbH), NaHya 3: Sodium salt of hyaluronic acid ($M_n$~200,000 Dalton, hyaluronic acid degraded with chlorine dioxide)

The hyaluronic acids were dissolved in phosphate buffer pH 7.4 to be at a concentration of 1% by weight each. A total of 5 mL each of the hyaluronic acid solutions were mixed with 100 μl β-propiolactone and stored at room temperature for 48 hours. In parallel, hyaluronic acid solutions not treated with β-propiolactone were also stored as controls. In an additional comparison, hyaluronic acid solutions not treated with β-propiolactone were sterilized with gamma radiation. The gamma sterilization of the hyaluronic acid solutions was done by BBF Sterilizationsservice GmbH using a $Co^{60}$ source at a dose of 25.2 kGy.

The hyaluronic acid solutions in unsterile condition had a pH value of 7.4, and the pH was also 7.4 after the sterilization with β-propiolactone. The hyaluronic acid solution sterilized with β-propiolactone show no discolouration whatsoever as compared to the unsterile hyaluronic acid solutions. Both the unsterile hyaluronic acid solutions and the hyaluronic acid solution sterilized with β-propiolactone were clear to the eye and colourless. In contrast, the hyaluronic acid solutions sterilized by gamma irradiation showed a slight yellow discolouration.

The molecular masses and the molecular mass distribution of the hyaluronic acid samples were determined by means of gel permeation chromatography using pullulan standards. A refractive index detector (RI detector) was used as the detector. The measures were done in duplicate using a GPC facility from Jasco.

| Polysaccharide solution | Condition | Mn RI | Mw RI | D RI |
|---|---|---|---|---|
| NaHya 1 | unsterile | 923,300 | 5,714,500 | 6.39 |
| | β-Propiolactone-sterilized | 1,078,900 | 6,493,300 | 6.60 |
| | Gamma-sterilized | 11,950 | 8,791 | 1.60 |
| NaHya 2 | unsterile | 1,283,600 | 6,577,900 | 5.23 |
| | β-Propiolactone-sterilized | 1,325,400 | 6,260,600 | 4.73 |
| | Gamma-sterilized | 10,250 | 7,587 | 1.56 |
| NaHya 3 | unsterile | 218,400 | 479,000 | 2.24 |
| | β-Propiolactone-sterilized | 216,100 | 485,200 | 2.25 |
| | Gamma-sterilized | 10,132 | 7,475 | 1.57 |

$M_n$: number average molar mass
$M_w$: weight average molar mass
D: Polydispersity The sterilization of the polysaccharide solutions with β-propiolactone did not effect polymer degradation. By comparison, gamma sterilization led to significant polymer degradation.

Example 3

The following polysaccharide derivatives were used in the experiments described hereinafter:

Sodium salt of carboxymethylcellulose ($M_w$~90,000 Dalton, Sigma-Aldrich), Hydroxyethylcellulose (60SH-4000, Shin-Etsu-Chemical. Co)

Solutions of the polysaccharides were produced using 30 mL phosphate buffer (pH value 7.4) each.

| Polysaccharide | Concentration of the polysaccharide in the phosphate buffer [wt. %] |
|---|---|
| Sodium salt of carboxymethylcellulose | 2.00 |
| Methylcellulose (60SH-4000) | 1.00 |

A total of 100 mg β-propiolactone were added to 5 mL of the polysaccharide solutions each, mixed, and stored at room temperature for 48 hours. Untreated polysaccharide solutions were used as control. For the viscosimetric measurements on the solutions, the solutions were diluted to a polysaccharide concentration of 0.2% by weight and 0.4% by weight. Due to the high degree of polymer degradation, the polysaccharide solutions sterilized by gamma irradiation were measured without diluting.

The hyaluronic acid solution sterilized with β-propiolactone show no discolouration whatsoever as compared to the unsterile polysaccharide solutions.

The diluted polysaccharide solutions were measured using an Ubbelohde viscosimeter (capillary I, K=0.010257) at 25° C. (5-fold measurement).

| Sample | Condition | Concentration [wt. %] % | kinematic viscosity [mm²/s] |
|---|---|---|---|
| Carboxymethyl-cellulose, sodium salt | unsterile | 0.4 | 2.311 ± 0.0004 |
| | β-Propiolactone-sterilized | 0.4 | 2.317 ± 0.002 |
| | Gamma-sterilized | 2.0 | 1.503 ± 0.001 |
| Hydroxyethyl-cellulose (60SH-4000) | unsterile | 0.2 | 3.659 ± 0.003 |
| | β-Propiolactone-sterilized | 0.2 | 3.590 ± 0.003 |
| | Gamma-sterilized | 1.0 | 1.169 ± 0.001 |

Remark: Methylcellulose solutions that were clear to the eye were used. However, it cannot be excluded that transparent gel particles may have been present in the methylcellulose solution. This might explain the slightly higher kinematic viscosity of the sterilized methylcellulose solution as compared to the non-sterilized methylcellulose solution. It is likely that there was a gel particle present in the sterilized methylcellulose solution.

The kinematic viscosity of the polysaccharide solutions sterilized with β-propiolactone is basically the same as the kinematic viscosity of the unsterile polysaccharide solutions. The sterilization of the polysaccharide solutions with β-propiolactone is not associated with polymer degradation. In contrast, gamma sterilization leads to considerable polymer degradation as is evident from the comparison of the kinematic viscosity of the gamma-sterilized polysaccharide solutions and the kinematic viscosity of the unsterile polysaccharide solutions.

The invention claimed is:

1. Method for sterilizing aqueous polysaccharide solutions, comprising:
    adding a β-lactone to an aqueous solution of a polysaccharide in the presence of a buffer, thereby forming a mixture; and
    storing the mixture at a temperature of 4° C. to 40° C. for a period of at least 24 hours, wherein the added β-lactone is present in the mixture in an amount greater than or equal to 0.5% by weight.

2. Method according to claim 1, wherein the β-lactone is selected from compounds (a1) that are represented by general formula (I),

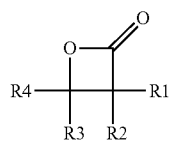

(I)

where R1, R2, R3, and R4, independently of each other, represent H, a substituted or non-substituted alkyl residue, halogen residue, nitro residue or cyano residue, and compounds (a2) that are selected from the group consisting of dimers of compounds (a1).

3. Method according to claim 2, wherein the β-lactone is β-propiolactone (CAS number 57-57-8).

4. Method according to claim 1, wherein the polysaccharide is selected from the group consisting of the sodium salt of hyaluronic acid, the sodium salt of carboxymethylcellulose, hydroxyethylcellulose, hydroxyethyl starch, methylcellulose, and oxidized cellulose.

5. Method according to claim 1, wherein phosphate buffer with a pH value of 7.0-8.0 is used as buffer system.

6. Method according to claim 5, wherein the phosphate buffer is selected from the group consisting of the combination of potassium hydrogenphosphate and disodium hydrogenphosphate, the combination of sodium hydrogenphosphate and disodium hydrogenphosphate, the combination of disodium phosphate and phosphoric acid, the combination of trisodium phosphate and sodium hydrogenphosphate, and the combination of trisodium phosphate and phosphoric acid.

7. Method according to claim 4, wherein the 3-hydroxypropionic acid produced by the hydrolysis of the β-propiolactone is a component of the buffer system.

8. Method according to claim 7, wherein the 3-hydroxypropanoic acid and the sodium salt of the hyaluronic acid or 3-hydroxypropanoic acid and the sodium salt of the carboxymethylcellulose form a buffer system.

9. Method according to claim 1, wherein all of the components of the buffer together are dissolved in the aqueous polysaccharide solution at a concentration of greater than or equal to 0.5% by weight.

10. Method according to claim 1, wherein the sterilization of the aqueous polysaccharide solution takes place inside a primary packaging means.

11. Method according to claim 10, wherein the aqueous polysaccharide solution and the β-lactone are mixed immediately before the aqueous polysaccharide solution is filled into the primary packaging means.

12. Method according to claim 1, wherein the aqueous solution comprises a buffer system whose buffering capacity is sufficient to buffer the 3-hydroxypropanoic acid generated by hydrolysis of the β-lactone such that the pH value of the sterilized aqueous polysaccharide solution is equal to that of the unsterilized polysaccharide solution.

13. Sterile polysaccharide solution produced according to the method of claim 1, wherein the aqueous polysaccharide solution comprises at least one polysaccharide that is at least partially soluble in water, in water and 3-hydroxypropionic acid, and in a buffer system.

14. Sterile polysaccharide solution according to claim 13, wherein the buffer system comprises sodium ions, dihydrogenphosphate ions, hydrogenphosphate ions, phosphate ions, 3-hydroxypropionic acid, and 3-hydroxypropionate.

15. A visco-supplementation or a pharmaceutical drug carrier in human and veterinary medicine, comprising a sterile polysaccharide solution produced with the method according to claim 1.

* * * * *